US006383766B1

(12) United States Patent
Warren et al.

(10) Patent No.: US 6,383,766 B1
(45) Date of Patent: May 7, 2002

(54) REDUCED CORTISOL CONJUGATES

(75) Inventors: Harold C. Warren, Rush; Brian A. Snyder, Rochedster; Lisa D. Sprague, Naples; Shirley Y. Lynn; Paul B. Contestable, both of Rochester; Holly L. Groth, Hamlin, all of NY (US)

(73) Assignee: Ortho-Clinical Diagnostics, Inc., Rochester, NY (US)

( * ) Notice: Subject to any disclaimer, the term of this patent is extended or adjusted under 35 U.S.C. 154(b) by 0 days.

(21) Appl. No.: 09/408,931

(22) Filed: Sep. 30, 1999

Related U.S. Application Data
(60) Provisional application No. 60/102,836, filed on Oct. 2, 1998.

(51) Int. Cl.[7] .................... G01N 33/535; C12N 9/96; C07K 16/26
(52) U.S. Cl. .................... 435/7.93; 435/7.5; 435/188; 436/532; 436/545; 436/546; 436/817; 530/388.24; 530/402; 530/404; 530/405; 530/406
(58) Field of Search ................ 435/188, 7.93, 435/7.5; 436/546, 545, 532, 817; 530/402, 404, 405, 406, 388.24

(56) References Cited

U.S. PATENT DOCUMENTS

| | | |
|---|---|---|
| 3,867,258 A | 2/1975 | Forgione |
| 3,992,158 A | 11/1976 | Przybylowicz et al. |
| 4,042,435 A | 8/1977 | Houck |
| 4,050,898 A | 9/1977 | Goffe et al. |
| 4,066,403 A | 1/1978 | Bruschi |
| 4,081,525 A * | 3/1978 | Knight et al. |
| 4,128,629 A * | 12/1978 | Eldred et al. |
| 4,153,668 A | 5/1979 | Hill et al. |
| 4,258,001 A | 3/1981 | Pierce et al. |
| 4,292,272 A | 9/1981 | Kitajima et al. |
| 4,372,745 A | 2/1983 | Mandle et al. |
| 4,430,436 A | 2/1984 | Koyama et al. |
| 4,483,921 A | 11/1984 | Cole |
| 4,517,288 A | 5/1985 | Giegel et al. |
| 4,670,381 A | 6/1987 | Frickey et al. |
| 4,822,747 A | 4/1989 | Johnson et al. |
| 4,824,778 A | 4/1989 | Nagai et al. |
| 4,829,012 A | 5/1989 | Cambiaso et al. |
| 4,839,299 A | 6/1989 | Charlton et al. |
| 4,847,194 A | 7/1989 | Quante |
| 4,847,195 A | 7/1989 | Khanna et al. |
| 4,853,335 A | 8/1989 | Olsen et al. |
| 4,855,226 A | 8/1989 | Polito et al. |
| 4,857,453 A | 8/1989 | Ullman et al. |
| 4,857,454 A | 8/1989 | Freundlich et al. |
| 4,859,610 A | 8/1989 | Maggio |
| 4,863,876 A | 9/1989 | Hevey |
| 4,868,106 A | 9/1989 | Ito et al. |
| 4,868,130 A | 9/1989 | Hargreaves |
| 4,879,219 A | 11/1989 | Wands et al. |
| 4,950,592 A | 8/1990 | Daiss |
| 5,338,671 A | 8/1994 | Scalice et al. |
| 5,599,720 A * | 2/1997 | Ekins |
| 5,616,503 A * | 4/1997 | Self |
| 5,650,324 A | 7/1997 | Gorman et al. |
| 5,663,054 A | 9/1997 | Williams et al. |
| 5,776,933 A | 7/1998 | Gordon et al. |
| 5,912,114 A * | 6/1999 | Hutchinson et al. |

FOREIGN PATENT DOCUMENTS

EP 0154902 B2 7/1999

OTHER PUBLICATIONS

Bovin, Nicolai V., "Polyacrylamide–Based Clycoconjugates As Tools in Glycobiology", Glyconjugate Journal, 1998, pp. 431–445, vol. 15.
Berke, "A Primer for Multilayer Immunoassay", American Chemical Society Conference Proceeding, 1988 pp. 303–312, Plenum Press.
Sommer et al., "Dry–Reagent Strips for Measuring Phenytoin in Serum", Clinical Chemistry, 1986, pp. 1770–1774, vol. 32.
Kaplan, Lawrence, A., Pesce, Amadeo, J., Clinical Chemistry: Theory, Analysis, and Correlation, 1989, pp. 673–674, CV Mosby Company.
Sommer et al., "A Unitized Enzyme–Labeled Immunometric Digoxin Assay Suitable for Rapid Testing", Clinical Chemistry, 1990, pp. 201–206, vol. 36/2.
Tietz, N.W., "Fundamentals of Clinical Chemistry", 1987, pp. 569–571, W.B. Saunders Company.
Saunders, George C., "The Art of Solid–Phase Enzyme Immunoassay Including Selected Protocols", Immunoassays in the Clinical Laboratory, Proceedings of the First Annual Conference Held at La Jolla, CA, Mar. 30–Apr. 1, 1978, pp. 100–118, Alan R. Liss, Inc., New York.
Tijssen, P., "Practice and Theory of Enzyme Immunoassays" Laboratory Techniques in Biochemistry and Molecular Biology, 1985, pp. 221–278, vol. 15, Elsevier.
Yoshitake, et al., Conjugation of Glucase Oxidase from Aspergillus niger and Rabbit Antibodies Using N–Hydroxyduccinimide Ester of N–(4–Caroboxycyclohexylmethyl)–Maleimide, 1979, pp. 395–399, vol. 101.
Weeman et al., "Enzyme Immunoassay of Hormones", Scandinavian Journal of Immunology, 1978, pp. 73–82, vol. 8, Suppl. 7, Blackwell Scientific Publications.

* cited by examiner

Primary Examiner—Mary E. Ceperley
(74) Attorney, Agent, or Firm—Stacey B. Antar

(57) ABSTRACT

The present invention relates to compositions comprising novel reduced cortisol conjugates, methods for their preparation and use in immunoassays for cortisol.

In another aspect, it relates to conjugates of reduced cortisol as immunogens or haptens for eliciting anti-cortisol or anti-reduced cortisol antibodies.

25 Claims, No Drawings

REDUCED CORTISOL CONJUGATES

This application claims benefit of application Ser. No. 60/102,836 filed Oct. 2, 1998.

FIELD OF THE INVENTION

The present invention relates to haptens and conjugate labels having improved specificity for anti-cortisol antibodies, methods for their preparation and use in immunoassays for the detection of cortisol. More particularly, the present invention relates to conjugates comprising horseradish peroxidase and reduced cortisol.

BACKGROUND OF THE INVENTION

Cortisol is the major glucocorticoid in humans. It is synthesized and secreted by the zona fasciculata and the zona reticularis of the adrenal cortex. It is involved in the regulation of carbohydrate, protein, and lipid metabolism. Cortisol levels can rise ten fold following surgery or other major trauma, as the steroid acts to prevent vascular collapse, reduce inflammation, and suppress the immune system.

There are three primary medical disorders associated with hyperadrenalism: Cushing's syndrome, hyperaldosteronism, and congenital adrenal hyperplasia. Cushing's syndrome is the term used to describe any condition resulting from an increased concentration of circulating glucocorticoid, usually cortisol (*Clinical Chemistry: Theory, Analysis, and Correlation*; Lawrence A. Kaplan, Amadeo J. Pesce, C V Mosby Company, 1989, pp 673–4).

The detection and quantification of cortisol in human serum, plasma or urine is required for proper diagnosis, treatment and follow-up of cortisol related conditions.

Competitive binding immunoassays for cortisol comprise anti-cortisol antibody, usually bound to an immobilized or immobilizable substrate and labeled cortisol, or labeled analogs (derivatives) of cortisol. It shall be understood that whenever reference is made to labeled cortisol, unless otherwise indicated, the term is intended to encompass labeled analogs (derivatives) of cortisol. Labeled cortisol competes with cortisol for a limited number of anti-cortisol antibody binding sites. Signal derived from free or bound labeled cortisol is determined as a measure of the amount of cortisol.

The sensitivity and specificity of an immunoassay for cortisol are dependent on the labeled cortisol. It is important that labeled cortisol effectively compete for the limited number of anti-cortisol binding sites with steroids structurally similar to cortisol that may be present in a sample. Otherwise, a clinically acceptable determination of the amount of cortisol in the sample will not be obtained.

Individuals having a deficiency of the enzyme 11β-hydroxylase, or who receive metyrapone will have greatly increased levels of 11-deoxycortisol, which is structurally similar to cortisol (*Fundamentals of Clinical Chemistry*, Tietz,N. W., W. B. Saunders Co., 1987,p 569) and potentially can compete with labeled cortisol for binding to anti-cortisol antibody. Other cortisol-like steroids that may be present in a sample, which potentially can compete with labeled cortisol for anti-cortisol antibody, include prednisolone, cortisone, and corticosterone. Such competition with labeled cortisol for anti-cortisol antibody is termed cross-reactivity.

Commercial cortisol assays can exhibit cross-reactivity with all the above-identified steroids. For example, a cross-reactivity with 11-deoxycortisol of greater than 10 percent has been observed; seriously compromising the accuracy of the assay for cortisol.

SUMMARY OF THE INVENTION

The problems associated with prior art assays for cortisol have been overcome using the conjugate labels described hereinbelow.

The present invention relates to compositions comprising novel reduced cortisol conjugates, methods for their preparation and use in immunoassays for cortisol.

In another aspect, it relates to conjugates of reduced cortisol as immunogens or haptens for eliciting anti-cortisol or anti-reduced cortisol antibodies.

It was found unexpectedly that labeled reduced cortisol conjugates of the present invention effectively compete with cortisol-like steroids for binding to anti-cortisol antibodies, thereby exhibiting significantly less cross-reactivity compared with prior art labeled cortisol conjugates. Immunoassays for cortisol comprising labeled reduced cortisol conjugates of the present invention exhibit both improved specificity and sensitivity for the determination of cortisol.

Accordingly, the present invention provides a reduced cortisol conjugate of formula:

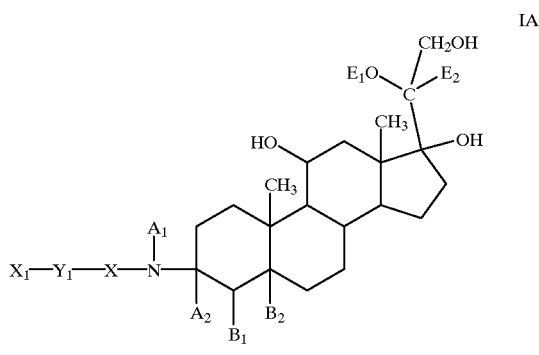

IA

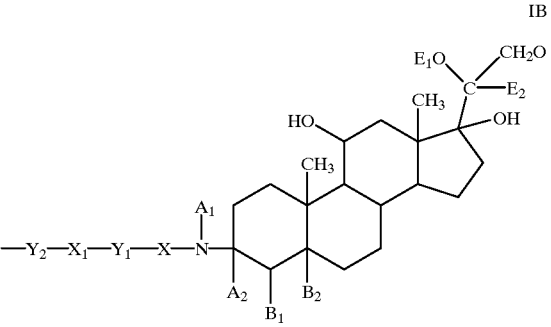

IB

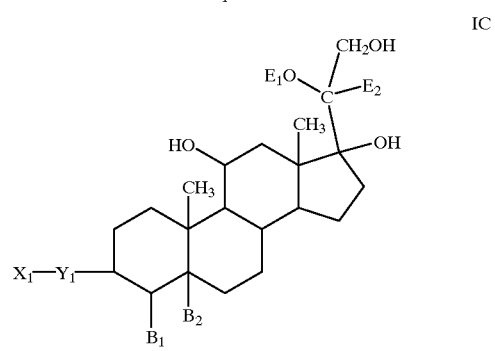

IC or

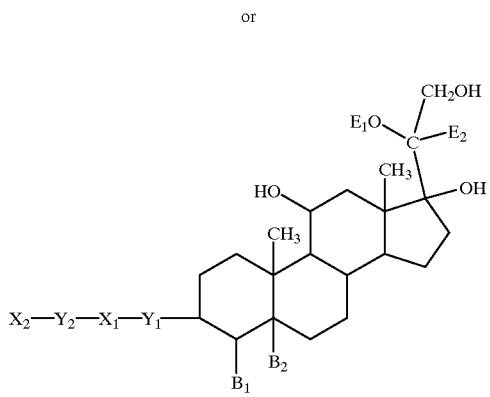
ID wherein X is O, S, sufonyl, or phosphono; $X_1$ is a labeled or unlabeled natural or synthetic polymer or a label; $Y_1$ is a linking group or a bond; $X_2$ is a labeled or unlabeled natural or synthetic polymer or a label; $Y_2$ is a linking group or a bond; $A_1$ and $A_2$ are each hydrogen or $A_1$ and $A_2$ together form a single bond, $B_1$ and $B_2$ are each hydrogen or $B_1$ and $B_2$ together form a single bond, $E_1$ and $E_2$ are each hydrogen or $E_1$ and $E_2$ together form a single bond provided at least one of $A_1$ and $A_2$, or $B_1$ and $B_2$, or $E_1$ and $E_2$ are each hydrogen.

In another aspect, the present invention relates to methods for the preparation of reduced cortisol conjugates. Accordingly, we provide a method for preparing a reduced cortisol conjugate of formula

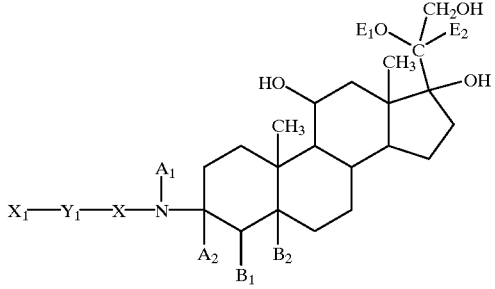
IA

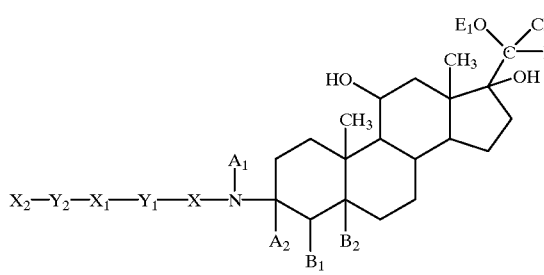
IB

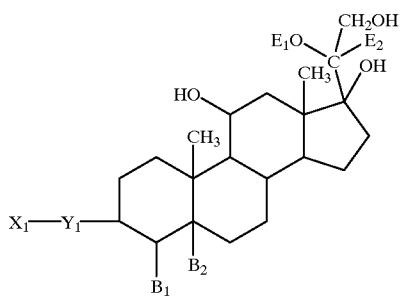
IC

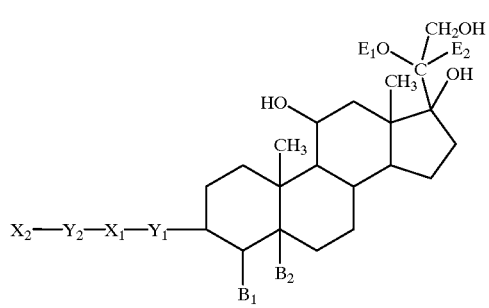
ID wherein X, $X_1$, $Y_1$, $X_2$, $Y_2$, $A_1$, $A_2$, $B_1$, $B_2$, $E_1$ and $E_2$ are as defined above, comprising:

reacting a compound of formula

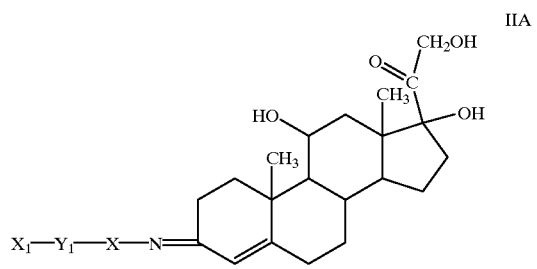
IIA

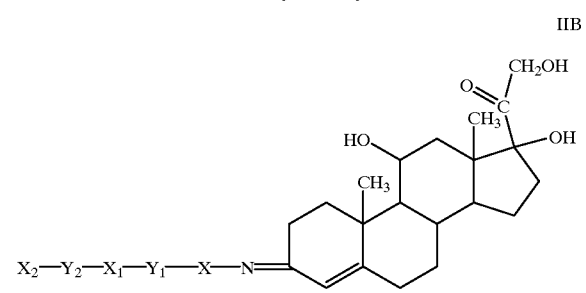
IIB

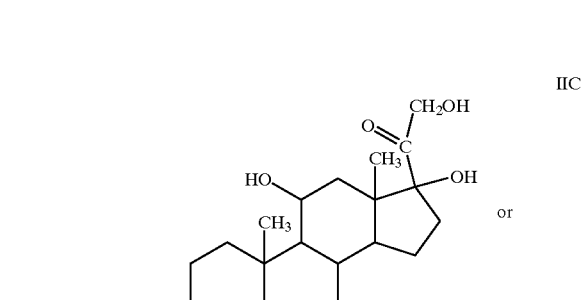
IIC

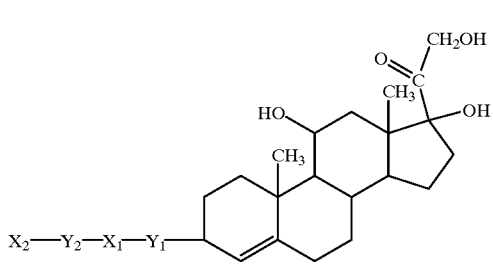

with a reducing agent.

An alternative method is provided for preparing a reduced cortisol conjugate of formula

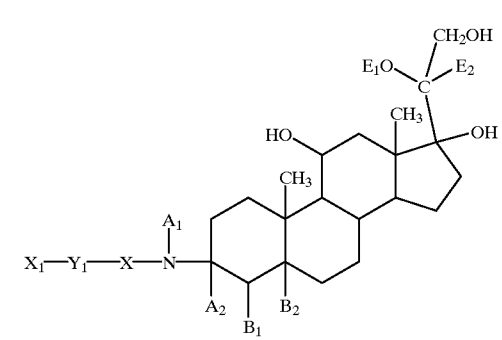

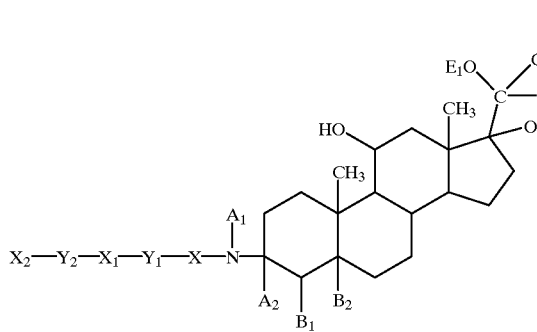

or

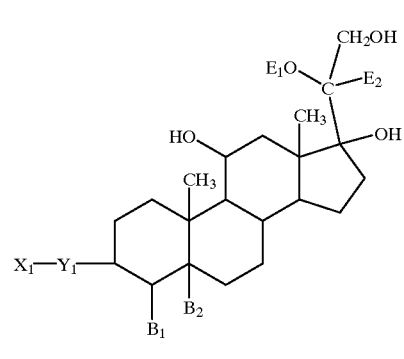

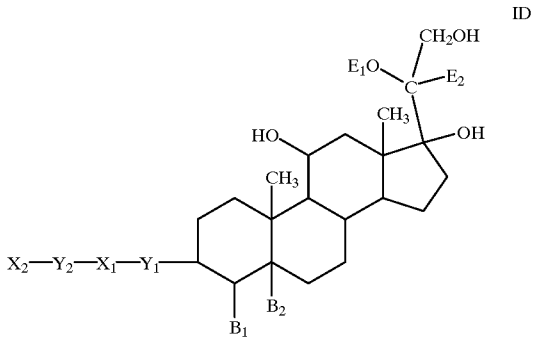

wherein X, $X_1$, $Y_1$, $X_2$, $Y_2$, $A_1$, $A_2$, $B_1$, $B_2$, $E_1$ and $E_2$ are as defined above, comprising the steps of:

(i) reacting a compound of formula

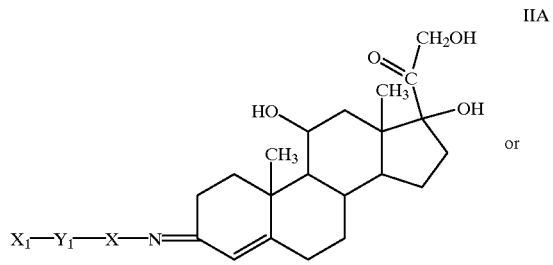

or

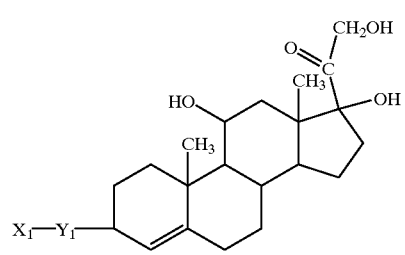

with a reducing agent, thereby forming compound IA or IC; and ii) with a first coupling agent, thereby forming a compound of formula

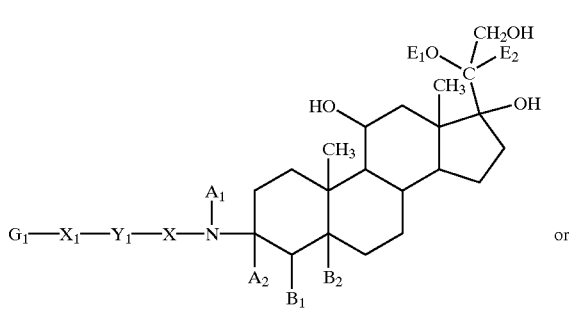

or

-continued

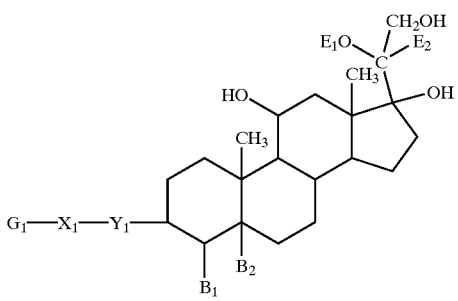

IIIC wherein $G_1$ is a coupling group;

(iii) optionally, reacting $X_2$ with a second coupling agent, thereby forming $X_2$—$G_2$, wherein $G_2$ is a coupling group capable of forming a covalent bond with the coupling group $G_1$, and wherein $G_1$ and $G_2$ may be the same;

(iv) optionally reacting compound IA or IC with $X_2$—$G_2$ wherein $G_2$ is capable of forming a covalent bond with a functional group of $X_1$, thereby forming reduced cortisol conjugate IB or ID;

(v) optionally reacting compound IIIA or IIIC with $X_2$ wherein $G_1$ is capable of forming a covalent bond with a functional group of $X_2$, thereby forming reduced cortisol conjugate IB or ID;

(vi) optionally reacting compound IIIA or IIIC with $X_2$—$G_2$, thereby forming reduced cortisol conjugate IB or ID.

In yet another aspect, the present invention relates to methods for the qualitative or quantitative determination of cortisol that utilize the novel labeled reduced cortisol conjugates.

Accordingly, we provide a method for performing a competitive assay for cortisol comprising the steps of:

A) contacting a sample suspected of containing cortisol with
  (i) an immobilized or immobilizable receptor that binds cortisol, thereby forming cortisol that is bound and cortisol that is not bound to the immobilized or immobilizable receptor,
  (ii) a labeled reduced cortisol conjugate of formula IA, IB, IC or ID as defined above, thereby forming labeled reduced cortisol conjugate that is bound and labeled reduced cortisol conjugate that is not bound to the immobilized or immobilizable receptor;

B) detecting either the labeled reduced cortisol conjugate that is bound or the labeled reduced cortisol conjugate that is not bound to the immobilized or immobilizable receptor as a measure of the amount of cortisol in the sample.

In an alternative ebodiment, the assay method described above may be combined with a step wherein the labeled reduced cortisol conjugate that is bound is separated from the labeled reduced cortisol conjugate that is not bound to the immobilized or immobilizable receptor;

An alternative method for performing a competitive assay for cortisol using a dry analytical element is also provided, the dry analytical element comprising a) a spreading zone,
b) one or more reagent zones,
c) a support, and together or separately in one or more of the zones, an immobilized receptor that binds cortisol and optionally, a labeled reduced cortisol conjugate of formula IA, IB, IC or ID defined above, wherein the method comprises the steps of:

A) contacting the spreading zone of the dry analytical element with
  i) a sample suspected of containing cortisol, thereby forming cortisol that is bound and cortisol that is not bound to the immobilized receptor,
  ii) labeled reduced cortisol conjugate if it is not present in the dry analytical element, thereby forming labeled reduced cortisol conjugate that is bound and labeled reduced cortisol conjugate that is not bound to the immobilized receptor, B) optionally, separating the labeled reduced cortisol conjugate that is bound from the labeled reduced cortisol conjugate that is not bound to the immobilized receptor; and C) detecting either the labeled reduced cortisol conjugate that is bound or the labeled reduced cortisol conjugate that is not bound to the immobilized receptor as a measure of the amount of cortisol in the sample.

In another sense, the present invention relates to haptens or immunogens of formula IA, IB, IC or ID as defined above and compositions comprising the immunogens. It also relates to methods of producing anti-cortisol antibodies using the immunogens of the present invention, by immunizing a host animal, removing blood from the host, and separating antibodies that bind cortisol from the host animal's blood serum or plasma. In another related method, the spleen, thymus or other organ that is populated with antibody producing cells is removed from the immunized host animal, antibody secreting hybridomas are prepared using antibody producing cells of the spleen, thymus or other organ so removed, and antibodies that bind cortisol are selected therefrom.

In yet another sense, the present invention relates to methods of reducing cross-reactivity in immunoassays for cortisol using labeled reduced cortisol conjugates of formula IA, IB, IC or ID.

The labeled reduced cortisol conjugates of the present invention, as stated, effectively compete with cortisol-like steroids for binding to anti-cortisol antibodies, thereby exhibiting significantly less cross-reactivity compared with prior art labeled cortisol conjugates.

DETAILED DESCRIPTION

The invention is described in detail with respect to a specific reduced cortisol conjugate comprising bovine serum albumin and horseradish peroxidase. This has been done to illustrate the present invention and is not intended in any way to limit the invention to this specific example. Other reduced cortisol conjugates, their syntheses and use as immunogens, or as reduced cortisol labels in competitive and noncompetitive immunoassay and in other aspects that are evident from the teachings presented herein or would be known to the skilled artisan are also contemplated.

A "natural polymer" for the purpose of the present invention is herein defined as one that originates from a biological source including but not limited to: microorganisms, fungi, viruses, human, cow, pig, mouse, cat, dog, rat, or insect. Such natural polymers include proteins, peptides, glycoproteins, lipoproteins and recombinant and chemically modified species thereof, polysaccharides, celluloses, collagens, and latexes. Somewhat more specific examples include, dextrans, porcine, human, mouse, rat and bovine serum albumins or globulins, strepavidin, antibodies, enzymes such as peroxidase, β-galactosidase, and alkaline phosphatase.

A "synthetic polymer" is defined herein as a polymer that does not necessarily directly originate from a biological source. It is one that is prepared by methods well known to the skilled artisan. For example, by way of monomer condensation using emulsion polymerization, ionic chain polymerization, carbonyl polymerization, radical chain polymerization and the like. It includes homopolymers such as polyacrylamides, polymethacrylates, polystyrenes, substitited polyacrylamides, polymethacrylates, and polystyrenes, and copolymers comprising two or more different monomeric units, such as acrylamide or substituted acrylamide, styrene and substituted styrene, and the like, as would be well known to one skilled in the art. It includes blockcopolymers, graftcopolymers, aqueous soluble and aqueous insoluble polymers and covalent and non-covalent combinations with natural polymers.

The term "label" as defined herein includes: chemical elements, compounds, and enzymes that are capable of being detected directly or indirectly using, for example, absorption, fluorescence, or reflectance spectrophotometry, or radiation detection methods. A label may be a natural or synthetic polymer. For example, horseradish peroxidase is both a label and a natural polymer. But a label is not necessarily a natural or synthetic polymer.

A label capable of direct detection is one that is intrinsically capable of producing a detectable signal. Such labels include organic and inorganic substances capable of fluorscence, or phosphoresence, such as but not limited to fluorescein, and derivatives thereof, and N-(3-fluoranthyl)-maleimide, radionucleides, such as carbon 14, tritium and phosporus 32, and the like. Included are substances having appropriate spectral absorption such as but not limited to, azo-oxo, azo-tetrazo, azine, oxazine, thiazine, quinoline, indamine, pyrone and pyrazolone dyes.

A label that is capable of indirect detection requires the presence of one or more additional substances for production of the detectable signal. Such labels typically include but are not limited to enzymes that require the presence of a substrate(s), co-factor(s), metal(s) and the like. Peroxidases, most particularly, horseradish peroxidase, a common label, requires an electron donor and an oxidizing agent, such as luminol, di- or triarylimidazole leucodyes and hydrogen peroxide to produce a chemiluminescent product or dye, respectively. Other enzymes, such as β-galactosidase, glucose oxidase and alkaline phosphatase, and the like, are also contemplated.

In general, labels include radioactive tags, enzymes, chromophores, fluorophores, stable free radicals, and enzyme cofactors, inhibitors and allosteric effectors.

A "reducing agent", for the purpose of the present invention, is any compound or reagent admixture that is capable of hydrogenating a double bond, such as carbon-carbon, carbon-nitrogen, carbon-oxygen and carbon-sulfur double bonds.

Useful reducing agents include but are not limited to: aluminum hydride, lithium aluminum hydride, borohydride and salts thereof. Catalytic hydrogenation over paladium, platinum or nickel or other hydrogenation methods can also be used. Sodium borohydride is a preferred reducing agent.

A "linking group" is defined herein, as a chemical group comprising one or more atoms. A linking group connects one molecule to another, such as a natural polymer to a natural polymer, a synthetic polymer to a synthetic polymer, a natural polymer to a synthetic polymer, a label to a natural or synthetic polymer, a label to reduced cortisol, a label to cortisol, and so on, through formation of a covalent bond with each of the molecules it joins.

The linking group can comprise a substituted or unsubstituted straight chain or branched alkyl or heteroalkyl, such as oxyalkyl, thioalkyl, aminoalkyl, substituted or unsubstituted alkenyl, one or more substituted or unsubstituted hydrocarbon heterocyclic rings, one or more substituted or unsubstituted aryl or heteroaryl rings such as but not limited to, imidazoyl, isoxazolyl, pyridyl, piperidyl, piperazinyl, pyrazolyl,triazolyl, oxadiazolyl, pyridazinyl, pyrimidyl, pyrazinyl, quinolinyl, and quinazolinyl.

Linking or coupling of macromolecules, such as natural and synthetic polymers to other macromolecules, or linking small molecules, such as cortisol or analogs of cortisol, to macromolecules is well known in the art. Specifically with respect to cortisol, carbon 3(C3)is reactive with nucleophiles including, amines, oximes, and thio-oximes and others known in the art. The nucleophilic species may be a coupling (linking) agent, a label, a natural or synthetic polymer. If it is a coupling agent or other species having a reactive functional group (a label, etc.), upon covalently bonding to the C3 of cortisol it may be reacted further with another coupling agent or other species having an appropriately reactive functional group. Cortisol so derivatized can be used as the starting point for preparing the reduced cortisol compounds of the instant invention. Details of coupling chemistry and linking groups may be found in numerous publications, including, U.S. Pat. Nos. 3,654,090; 3,791,932; 3,875,011; 4,016,043; 4,040,907; 4,092,479; 4,213,894; 4,243,749; 4,376,165; 4,410,643; 4,752,658; 4,828,978; 4,879,249; 4,997,772; 5,053,497; 5,106,732; 5,147,777; 5,155,166; 5,162,219; 5,177,023; 5,284,948; 5,298,403; 5,308,749; 5,374,516; 5,391,483; 5,397,695; 5,401,633; 5,527,709; 5,543,311; 5,578,457; 5,652,346; 5,763,588; 5,770,390 and references identified therein; Yoshitake et al. Eur. J. Biochem., 101, 395, (1979) and Tjssen, in *Laboratory Techniques in Biochemistry and Molecular Biology*, pp 221–278 (1985) and references therein.

In brief, a linking group and molecule to which it is covalently attached can be connected through amide, ester, ether, thioester, and disulfide bonds. For example coupling or linking chemistry that includes reacting the molecules to be coupled with condensing agents such as carbodiimides, maleimides, ethylchloroformate, and glutaraldehyde is well known in the art.

The term "sample" refers to any substance that may contain the analyte of interest. A sample can be a biological fluid, such as cerebral spinal fluid, semen, vaginal secretions, sputum, ascites fluid, lacrimal fluid, sweat, serum, plasma, urine, whole blood or whole blood components including red and white blood cells, platelets, and other fluids or tissues of the body that may contain the analyte of interest. Optionally, samples may be obtained from water, soil and plants.

Immunoassays, which take advantage of natural immunological reactions, have found wide-spread use as analytical techniques in clinical chemistry. Because of the specificity of the reactions, they are particularly advantageous in quantifying biological analytes, that are present in very low concentration in biological fluids. Such analytes include, for example, antibodies, therapeutic drugs, narcotics, enzymes, hormones, proteins, etc.

In competitive binding immunoassays, a labeled analyte (the term includes immunocompetent analogs of the analyte) is placed in competition with unlabeled analyte for reaction with a fixed amount of an appropriate receptor, which is often immobilized on a solid susbstrate, or is capable of immobilization thereto. The labeled analyte that is bound to the receptor is separated from free labeled analyte. Unknown concentrations of the analyte can be determined from the measured signal of either the bound or free labeled analyte. The reaction proceeds as follows:

Analyte+labeled analyte+receptor⇌analyte–receptor+labeled analyte–receptor.

Immunoassays can be carried out in solution, in test devices where soluble and insoluble components can be separated, or in dry analytical elements. Immunoassays can be heterogeneous or homogeneous as those terms are known in the art. In heterogeneous assays, bound and free labeled immunoreactants (labeled analyte or labeled receptor for an analyte) are separated prior to signal measurement; whereas, in homogeneous assays separation of free from bound labeled immunoreactant is not required. The reduced cortisol conjugates of the instant invention can used in both homogeneous and heterogeneous assays.

Numerous publications relating to immunoassays and immunoassay methods, which include many of the above-cited publications relating to linking groups and coupling chemistry, are available to the practitioner. Additional publications include: U.S. Pat. Nos. 4,372,745; 4,670,381; 4,483,921; 4,517,288; 4,822,747; 4,824,778; 4,829,012; 4,839,299; 4,847,194; 4,847,195; 4,853,335; 4,855,226; 4,857,453; 4,857,454; 4,859,610; 4,863,876; 4,868,106; 4,868,130; 4,879,219; 5,663,054; 5,776,933 and all references cited therein; and *Immunoassays in the Clinical Laboratory,* Nakamura et al, eds., Alan R. Liss, Inc., (1979); *Quantitative Enzyme Immunoassay,* Engvall et al., eds, Blackwell Scientific Publications, (1978; *Clinical Chemistry,* Sommer et al., v.32,p. 1770–1774, (1986); *Clinical Chemistry,* Sommeret al., p 201–206 (1990); *A Primer for Multilayer Immunoassay,* Berke, American Chemical Society Conference Proceeding, p.303–312, Plenum Press, (1988); and all references cited therein.

In competitive immunoassays labeled analyte and sample containing free analyte can be added simultaneously or separately to an admixture comprising immobilized or immobilizable receptor that binds the analyte.

In the case of dry analytical elements, labeled analyte and immobilized receptor when present together in the element prior to contact with sample, are preferably present in separate zones.

Conventional materials and means for assembling dry-film analytical elements are described, for example, in U.S. Pat. Nos. 3,867,258; 3,992,158; 4,042,435; 4,050,898; 4,066,403; 4,153,668; 4,258,001; 4,292,272 and 4,430,436.

Methods to obtain antibodies that bind a specific molecule by immunizing suitable host animals is well known. Such methods are well documented and are described, for example, in the following publications: *Methods in Immunology,* Garvey,J. S., Cremer,N. E. and Sussdorf,D. H., W. A. Benjamin,Inc., Third Ed. (1977)and *Handbook of Experimental Immunology,* edited by Weir,D. M., Blackwell Scientific Publications, Third Ed., (1978)

Methods of producing hybridoma cell lines for secretion of antibodies is also well known, and are provided, for example, in U.S. Pat. Nos. 4,950,592; 5,338,671 and 5,650, 324.

Preparation of HRP Labeled Reduced Cortisol-3-CMO-BSA

A method is provided below illustrating the preparation of a horseradish peroxidase (HRP) labeled reduced cortisol conjugate. In this method the reduction of a bovine serum albumin cortisol oxime conjugate (Cortisol-3-CMO-BSA) with sodium borohydride was carried out prior to conjugation with HRP; however, reduction of cortisol can be carried out subsequent to coupling with HRP.

There are three sites for reduction of Cortisol-3-CMO-BSA that are marked by an asterisk in the structure shown below

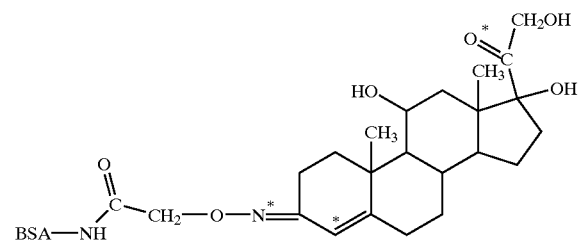

Any or all of these sites can be reduced by treatment with a reducing agent or reducing admixture that is capable of hydrogenating a double bond, yielding products having a single site reduced as in the structures shown below.

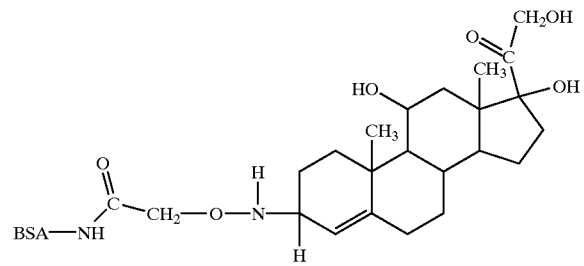

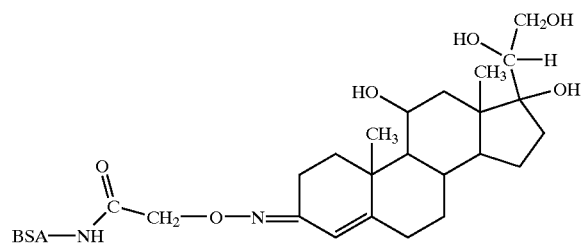

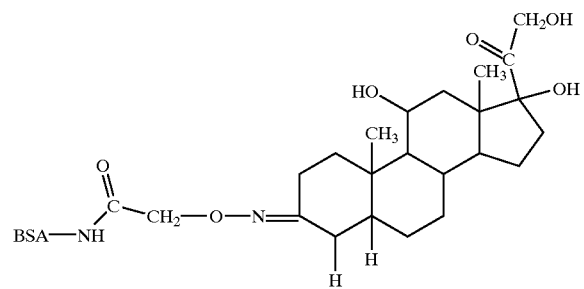

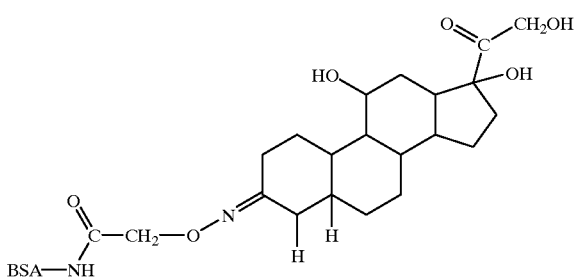

as well as, compounds having any two of the sites reduced, yielding three different reduced species, and all three sites reduced, is as readily apparent to the skilled artisan. Other conjugates comprising cortisol, which upon reduction produce the compounds generically defined in structures 1A, 1B, 1C and 1D, analogously will form different reduced cortisol species as exemplified above with Cortisol-3-CMO-BSA. Compounds having a covalent bond to C3 of cortisol that is not capable of being hydrogenated will be reduced only at the ring carbon-carbon double bond and/or the carbon-oxygen double bond (carbonyl group) of cortisol. All reduced forms individually or in any combination are contemplated in the present invention.

EXAMPLE 1
Preparation of 3-Cortisolcarboxymethyl Oxime Conjugated to Bovine Serum Albumin (3-CMO-BSA)

Hydrocortisone-3-(O-Carboxymethyl)oxime

Bovine Serum Albumin (Cortisol-3-CMO-BSA) was prepared as described below. Alternatively, it can be purchased from Sigma Chemical Co., St. Louis, Mo.

A stock solution of N-hydroxysuccimide (NHS) was prepared by dissolving 20 mg of NHS in 3.0 mL of dioxane. A stock solution of dicyclohexylcarbodiimide (DCC) was also prepared by dissolving 30 mg of DCC in 2.50 ml of dioxane. To a glass vial containing 40 mg of Cortisol-3-carboxymethyl oxime (Cortisol-3-CMO) was added 1.744 mL of the NHS stock and 1.744 mL of the DCC stock. The mixture was stirred and incubated for three hours at ambient room temperature. To 1.00 gram of Bovine Serum Albumin (BSA) was added 12 mL of 0.1M sodium hydrogen carbonate solution. The solution was mixed until clear and at the end of the three hour incubation, 3.0 ml of the activated Cortisol-3-CMO was added to the BSA solution. The mixture was stirred and incubated at ambient temperature for two hours. After the two hour incubation, 15 mL of 0.1M sodium phosphate, 0.3M sodium chloride (pH 6.0) buffer was added. The mixture was filtered through a 5.0 um and 0.45 um Sartorius Minisarts and then cromatographed on a 5x70 cm Superdex 200PG column at a flow rate of 8.0 mL/min. The first tube corresponding to the major peak and the following ten (one minute) fractions were collected and pooled. Pool the fractions. The pooled fractions were dialyzed against water for approximately fifteen hours. The dialysis was repeated. The dialysate was filtered through a 0.2 um Sartorius Minsart and lyophilized in small aliquots and kept frozen until needed.

EXAMPLE 2
Reduction and Activation of Cortisol-3-CMO-BSA

Cortisol-3-CMO-BSA (24 mg) was dissolved in 4 mL of a solution of 50 mM sodium carbonate and 100 mM sodium chloride at pH 9.5. An aliquot, 0.60 mL, of an aqueous solution of sodium borohydride (4 mg per mL) was added to the cortisol-3-CMO-BSA solution, which was then mixed continuously for thirty minutes at 20° C. The pH was then adjusted, using about 200 μL of a 0.5 M sodium phosphate solution, to a value in a range between pH 7.2 to 7.5 to decompose any excess borohydride. The solution was gently mixed until effervescence ceased and allowed to stand for about fifteen minutes. The reaction mixture was then filtered through a 0.45μ filter and chromatographed on a Sephadex G25 1.6×14.5 cm column pre-equilibrated with 0.02 M phosphate, pH 7.0, at a flow rate of about 40 mL/hr. The fraction size collected was about 0.67 mL (1 min). Fifteen of the most concentrated fractions, that is, those fractions having a large absorption at 280 nm were pooled.

Succinimidyl 4-(N-maleimidomethyl) cyclohexane-1-carboxylate (SMCC) was dissolved in N,N-dimethylformamide (DMF) at a final concentration of 9.6 mg/mL. To 10 mL of the reduced cortisol-3-CMO-BSA collected from the chromatography step above, was added 186 μL of the SMCC solution. The solution was mixed gently then incubated for one hour at 20° C. The reaction was quenched with 800 μL of an aqueous solution of glycine (10 percent, weight/voume). The quenched reaction mixture was then chromatographed on a 3.2×10 cm column filled with Sephadex G25 pre-equilibrated with a solution of 0.1 M phosphate and 5 mM ethylenediaminetetraacetic acid (EDTA), pH 6.0, at a flow rate of about 161 mL/hr. One milliliter fractions were collected. Eight of the most concentrated fractions (having a large absorption at 280 nm) were pooled and used for conjugation to activated HRP.

EXAMPLE 3
Activation of HRP

Horseradish peroxidase was dissolved in 0.1 M phosphate, pH 7.5, at a final HRP concentration of 10 mg/mL. Five milliliters of the HRP solution were transferred to a 20 mL reaction vial. A 0.5 mL aliquot of S-acetylthioacetic acid, N-hydroxysuccinimidyl ester (SATA) in DMF (25 mg/mL) was added to the reaction vial containing the HRP solution. The solution was mixed gently then incubated at 20° C. for sixty minutes. An aliquot (500 μL) of a solution containing 0.05 M EDTA and 2.5 M hydroxylamine at pH 7.0, was added to the reaction mixture, mixed gently, and then incubated at 20° C. for 15 minutes. The mixture was then chromatographed on a 2.0×10 cm column of Sephadex G25 pre-equilibrated with a solution of 0.1 M phosphate and 5 mM EDTA at pH 6.0, using a flow rate of about 63 mL per hour. One minute fractions were collected. Eleven of the most concentrated fractions (having a large absorption at 403 nm) were pooled.

EXAMPLE 4
Coupling of Activated HRP and Reduced and Activated Cortisol-3-CMO-BSA The activated, reduced cortisol-3-CMO-BSA 21.47 mL was combined with 11.55 mL of activated HRP. The solution was mixed gently, and incubated at 20° C. for twenty hours. An aliquot (224 μL) of a solution containing mercaptoethanol in water (1 percent of the thiol by volume) was added to the reaction mixture and the solution was mixed gently and allowed to stand for about 15 minutes. A 476 μL aliquot of a solution containing 10 mg/mL N-ethylmaleimide in DMF, was then added to the reaction mixture, and incubated an additional twenty minutes after mixing. The reaction mixture was then chromatographed on a 4.4×50 cm column containing Superdex 200 pre-equilibrated with a solution of 0.1 M phosphate and 0.3 M NaCl at pH 6.0 using a flow rate of about 344 mL per hour. One minute fractions were collected. Twenty six of the most concentrated fractions centered around the first eluates having a maximum absorption at 280 nm were pooled.

The absorption of the conjugate pool (cj) and the HRP solution (in Example 2 above, prior to activation and sufficiently diluted in phosphate buffer to obtain an accurate absorption measurement) were determined at 280 nm and 403 nm, $A_{403}cj$, $A_{280}cj$ and $A_{403}$ HRP, $A_{280}$ HRP respectively. The concentration of the reduced cortisol-3-CMO-BSA-HRP conjugate based on the BSA concentration was determined from these measurements using the following formula:

$$BSA(mg/mL) = A_{280}cj - (A_{403}cj/[A_{403}HRP/A_{280}HRP])/0.76$$

EXAMPLE 4
Evaluation of Conjugate

Evaluation of the HRP labeled reduced cortisol-3-CMO-BSA (hereinafter referred to as HRP-RC conjugate) was evaluated using an Ortho-Clinical Diagnostic VITROS ECi chemiluminesence-based assay methodology.

The following reagents were prepared for use with the VITROS ECi system.
Label Solution
    100 ng/mL reduced cortisol-3-CMO-BSA-HRP (or 20 ng/mL of a comparative HRP-cortisol conjugate label, which is not a conjugate label of the present invention, but which was carried through the same procedures as the label of the invention except for the reduction step)
    2.86 g/L sodium phosphate dibasic, anhydrous
    7.3 g/L sodium phosphate monobasic, monohydrate
    0.01 g/L potassium ferricyanide
    2.5 g/L 8-anilino-1-naphthalenesulfonic acid
    20 g/L bovine serum slbumin
    0.03 g/L apo-horseradish peroxidase
    0.2% bovine alpha globulin(Cohn fraction IV-I)
    1 g/L bovine gamma globulin
    5 g/L normal sheep serum
    100 g/L charcoal stripped human plasma
    20 g/L Kathon (a preservative comprising 5-chloro-2-methyl-4-isothiazolin-3-one and 2-methyl-4-isothiazolin-3-one)
    pH 6.4
Biotinylated Sheep Polyclonal Anti-Cortisol Solution
    1.5 μg/mL biotinylated sheep anti-cortisol gamma globulin
    21 g/L sodium phosphate dibasic, anhydrous
    1.8 g/L sodium chloride
    1.1 g/L citric acid
    20 g/L bovine serum albumin
    20 g/L Kathon
    pH 5.4
Wash Reagent
    0.39 g/L boric acid
    0.35 g/L disodium tetraborate
    0.58 g/L sodium chloride
    0.50 g/L TRITON X-100 (octylphenoxypolyethoxy ethanol)
    0.5% w/w BRONIDOX (a preservative comprising 5-bromo-5-nitro-1,3-dioxane)
    pH 8.4
Signal Reagent
Part A
    3.88 g/L boric acid
    14.2 g/L sodium tetraborate
    1.06 g/L sodium citrate
    0.08 g/L sodium benzoate
    0.10 g/L sodium azide
    0.008 g/L diethylenetriaminepentaacetic acid
    0.58 g/L glycine
    0.40 g/L luminol
Part B
    0.90 g/L citric acid
    1.68 g/L sodium citrate
    0.08 g/L sodium benzoate
    0.62 g/L sodium perborate
    0.06 g/L 3-chloro-4-hydroxyacetanilide
    5.84 g/L sodium chloride An aliquot (75 μL) of anti-cortisol biotinylated sheep antibody, 30 μL of sample, serum comprising cortisol or a steroid structurally similar to cortisol (below), and 75 μL of HRP-RC conjugate were added to an VITROS ECi sample container to which strepavidin had been prebound. The solution was incubated at 37° C. for 30 minutes, then washed using the above-indicated wash reagent.

A 200 μL aliquot of the above-indicated signal reagent solution (100 μL of part A and 100 μL of part B combined just prior to use) was then added to the sample container. The solution was incubated for 5 minutes at 37° C., and the chemiluminesence intensity was then determined.

EXAMPLE 5
Cross Reactivity

The above method was used to determine the concentration of potential cross reactant (steroid that is structurally similar to cortisol: 11-deoxycortisol, prednisolone, corticosterone and cortisone) that displaced fifty percent of a fixed amount of a comparative HRP labeled cortisol conjugate (nonreduced cortisol, HRP-NRC) or HRP-RC conjugate bound to a fixed amount of anti-cortisol antibody.

Varied levels of the potential cross reactant were added to sample containers containing either the comparative labeled cortisol conjugate (nonreduced cortisol, HRP-NRC) or HRP-RC conjugate of the instant invention, as described above.

The concentration of cross reactant resulting in a light signal measurement corresponding to 50% of the maximum attainable (all conjugate displaced) was determined and used to calculate the percent cross reactivity as described below and whose results are listed in Table 1.

Percent cross-reactivity is defined as The concentration of cortisol that displaced 50% of the HRP-NRC comparative conjugate (or the HRP-RC conjugate) divided by the concentration of cross-reactant that displaced 50% of the HRP-NRC comparative conjugate (or the HRP-RC conjugate) multiplied by 100 as determined per the assay method described hereinabove.

TABLE 1

| | Percent Cross-Reactivity | |
| --- | --- | --- |
| Compound | HRP-NRC Comparative Label | HRP-RC Invention Label |
| cortisol | 100 | 100 |
| prednisolone | 34.8 | 24.6 |

TABLE 1-continued

| | Percent Cross-Reactivity | |
|---|---|---|
| Compound | HRP-NRC Comparative Label | HRP-RC Invention Label |
| 11-deoxycortisol | 28.4 | 2.2 |
| cortisone | 5.5 | 1.8 |
| corticosterone | 4.4 | 3.3 |

These data clearly show that the representative HRP-RC conjugate of the present invention provides significantly less cross-reactivity in an immunoassay for cortisol. Accordingly, cortisol assays utilizing labeled reduced cortisol as described in the present invention will exhibit improved accuracy; resulting in improved diagnosis, treatment and follow-up.

The present invention has been described in detail with particular reference to certain preferred embodiments thereof. It will be understood that variations and modifications can be effected within the spirit and scope of the invention. All cited publications are incorporated herein by reference.

We claim:

1. A reduced cortisol conjugate of formula:

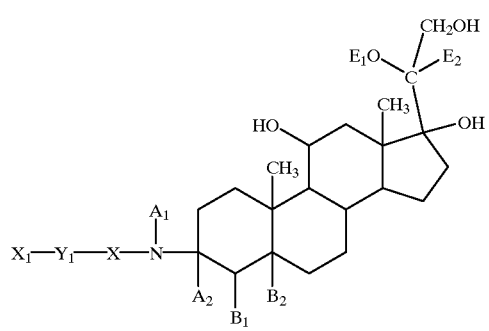

IA

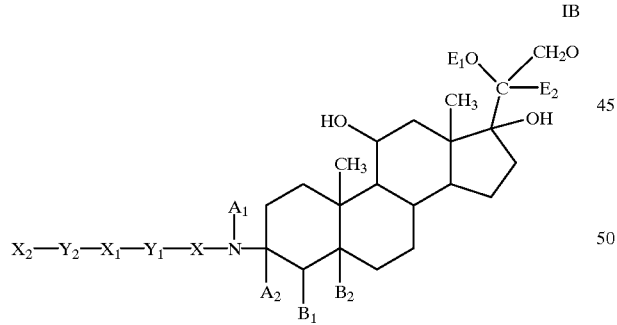

IB

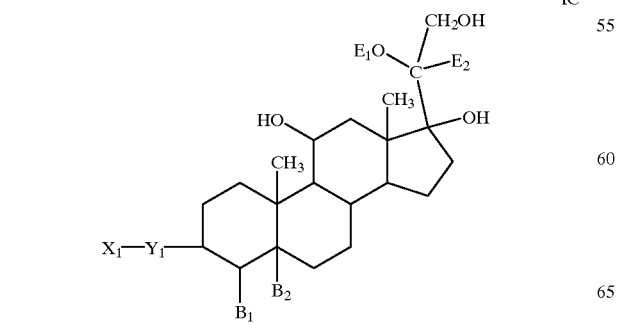

IC

-continued

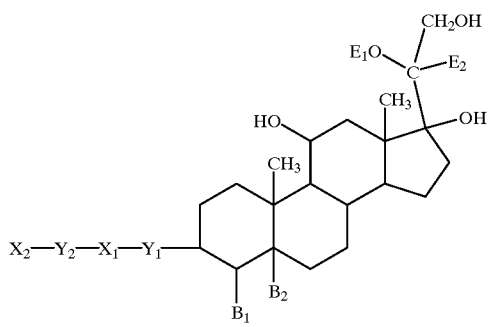

ID wherein X is O, S, sufonyl, or phosphono; $X_1$ is a labeled or unlabeled natural or synthetic polymer or a label; $Y_1$ is a linking group or a bond; $X_2$ is a labeled or unlabeled natural or synthetic polymer or a label; $Y_2$ is a linking group or a bond; $A_1$ and $A_2$ are each hydrogen or $A_1$ and $A_2$ together form a single bond, $B_1$ and $B_2$ are each hydrogen or $B_1$ and $B_2$ together form a single bond, $E_1$ and $E_2$ are each hydrogen or $E_1$ and $E_2$ together form a single bond provided at least one of $A_1$ and $A_2$, or $B_1$ and $B_2$, or $E_1$ and $E_2$ are each hydrogen.

2. The reduced cortisol conjugate of claim 1 wherein X is O, and $X_1$ is bovine serum albumin.

3. The reduced cortisol conjugate of claim 2 wherein $Y_1$ is methylenecarbonyloxy.

4. The reduced cortisol conjugate of claim 3 wherein $X_2$ is a peroxidase and $Y_2$ is (4-[2,5-dioxo-3-{(2-ethylcarbonyl)sulfanyl}tetrahydro-1H-1-pyrrolyl]methyl)-1-cyclohexanecarbonyl.

5. The conjugate of claim 1 in an aqueous composition.

6. A method for preparing a reduced cortisol conjugate of formula:

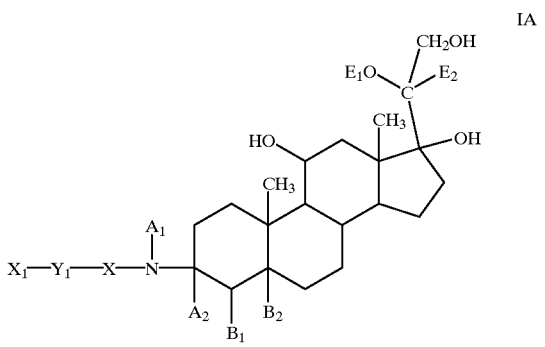

IA

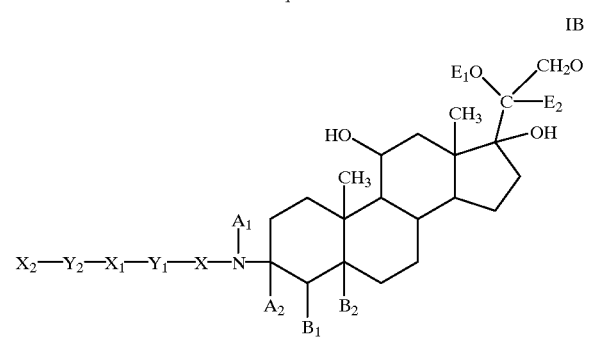

IB

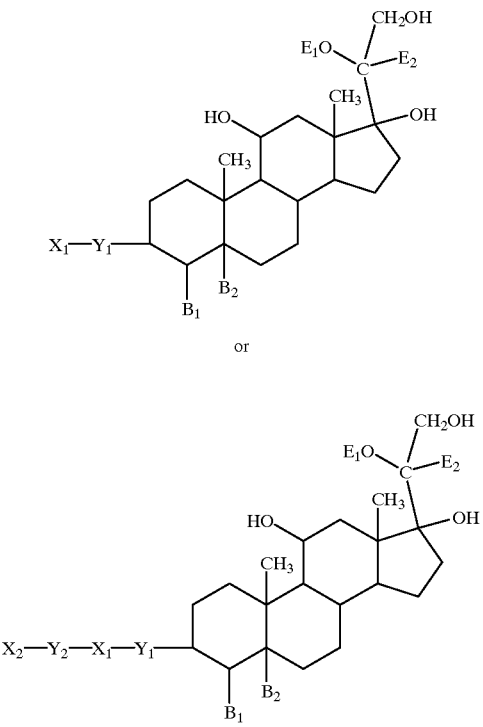

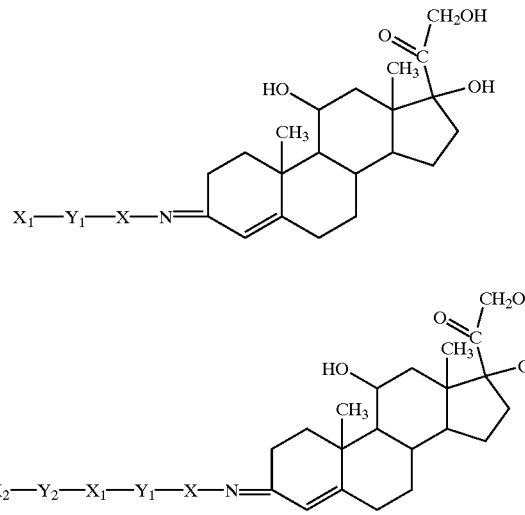

wherein X is O, S, sulfonyl, or phosphono; X1 is a labeled or unlabeled natural or synthetic polymer or a label; Y1 is a linking group or a bond; X2 is a labeled or unlabeled natural or synthetic polymer or a label; Y2 is a linking group or a bond; A1 and A2 are each hydrogen or A1 and A2 together form a single bond, B1 and B2 are each hydrogen or B1 and B2 together form a single bond, E1 and E2 are each hydrogen or E1 and E2 together form a single bond provided at least one of A1 and A2, or B1 and B2, or E1 and E2 are each hydrogen, comprising: reacting a a compound of formula

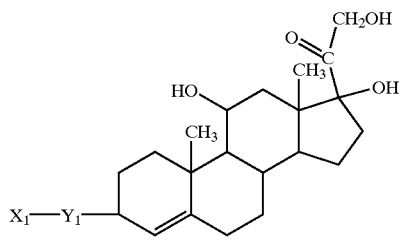

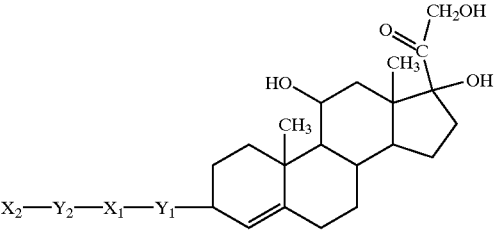

with a reducing agent.

7. The method of claim 6 wherein the reducing agent is a borohydride salt.

8. The method of claim 7 wherein X is O, $X_1$ is bovine serum albumin and $Y_1$ is methylenecarbonyloxy.

9. The method of claim 8 wherein $X_2$ is a peroxidase.

10. The method of claim 9 wherein $Y_2$ is (4-[2,5-dioxo-3-{(2-ethylcarbonyl)sulfanyl}tetrahydro-1H-1-pyrrolyl]methyl)-1-cyclohexanecarbonyl and $X_2$ is horseradish peroxidase.

11. A method for preparing a reduced cortisol conjugate of formula

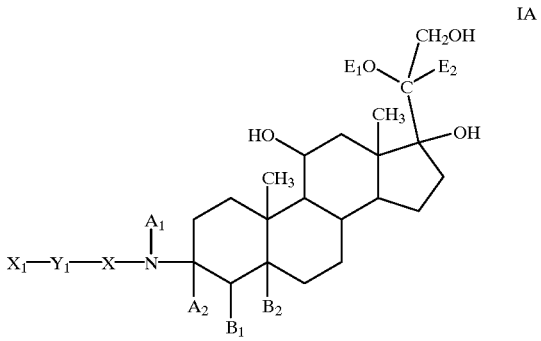

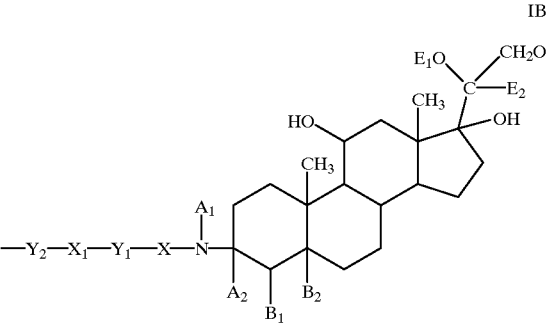

wherein X is O, S, sufonyl, or phosphono; $X_1$ is a labeled or unlabeled natural or synthetic polymer or a label; $Y_1$ is a linking group or a bond; $X_2$ is a labeled or unlabeled natural or synthetic polymer or a label; $Y_2$ is a linking group or a bond; $A_1$ and $A_2$ are each hydrogen or $A_1$ and $A_2$ together form a single bond, $B_1$ and $B_2$ are each hydrogen or $B_1$ and $B_2$ together form a single bond, $E_1$ and $E_2$ are each hydrogen or $E_1$ and $E_2$ together form a single bond provided at least one of $A_1$ and $A_2$, or $B_1$ and $B_2$, or $E_1$ and $E_2$ are each hydrogen, comprising the steps of:

(i) reacting a compound of formula

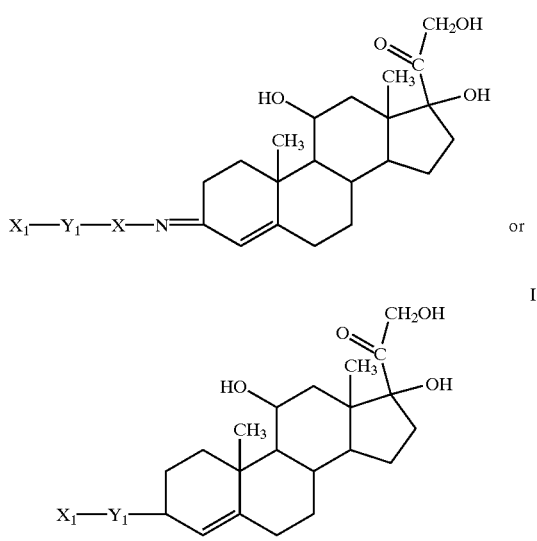

with a reducing agent, thereby forming compound IA or IC; and (ii) optionally, reacting compound IA or IC with a first coupling agent, thereby forming a compound of formula

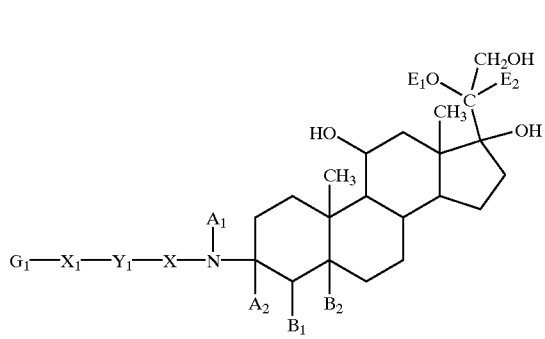

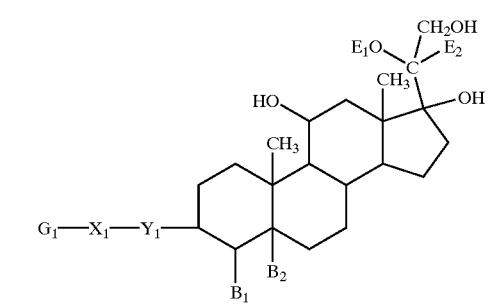

wherein $G_1$ is a coupling group;

(iii) optionally, reacting $X_2$ with a second coupling agent, thereby forming $X_2$—$G_2$, wherein $G_2$ is a coupling group capable of forming a covalent bond with the coupling group $G_1$, and wherein $G_1$ and $G_2$ may be the same;

(iv) optionally reacting compound IA or IC with $X_2$—$G_2$ wherein $G_2$ is capable of forming a covalent bond with a functional group of $X_1$, thereby forming reduced cortisol conjugate IB or ID;

(v) optionally reacting compound IIIA or IIIC with $X_2$ wherein $G_1$ is capable of forming a covalent bond with a functional group of $X_2$, thereby forming reduced cortisol conjugate IB or ID;

(vi) optionally reacting compound IIIA or IIIC with $X_2$—$G_2$, thereby forming reduced cortisol conjugate IB or ID.

12. The method of claim 11 wherein X is O, $X_1$ is bovine serum albumin.

13. The method of claim 12 wherein $Y_1$ is methylenecarbonyloxy.

14. The method of claim 13 wherein $X_2$ is a peroxidase, the first coupling agent is 4-(N-maleimidomethyl)-cyclohexane-1-carboxylic acid N-hydroxysuccinimide ester, and the second coupling agent is S-acetylthioacetic acid N-hydroxysuccinimidyl ester.

15. A method for performing a competitive assay for cortisol comprising the steps of:

A) contacting a sample suspected of containing cortisol with
  i) an immobilized or immobilizable receptor that binds cortisol, thereby forming cortisol that is bound and cortisol that is not bound to the immobilized or immobilizable receptor,
  ii) a labeled reduced cortisol conjugate of formula

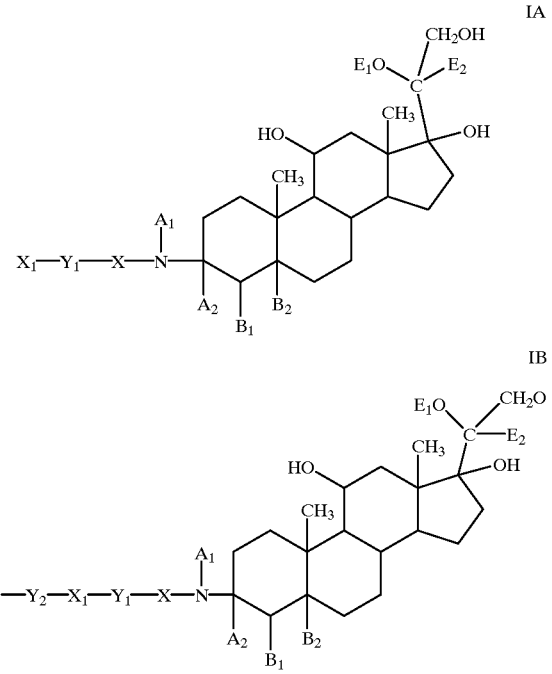

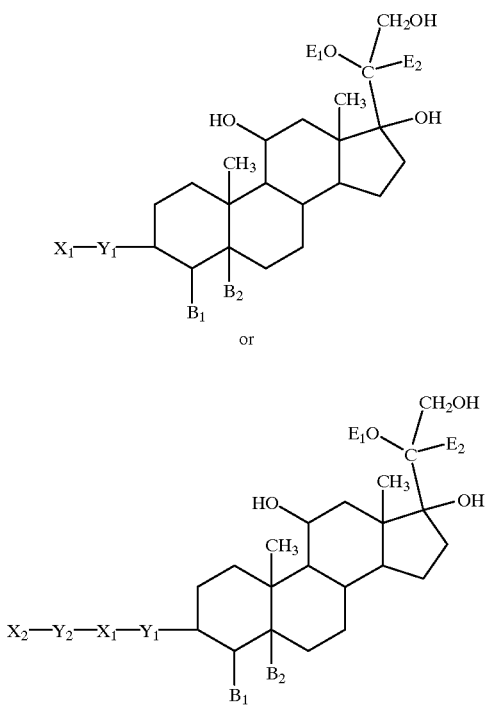

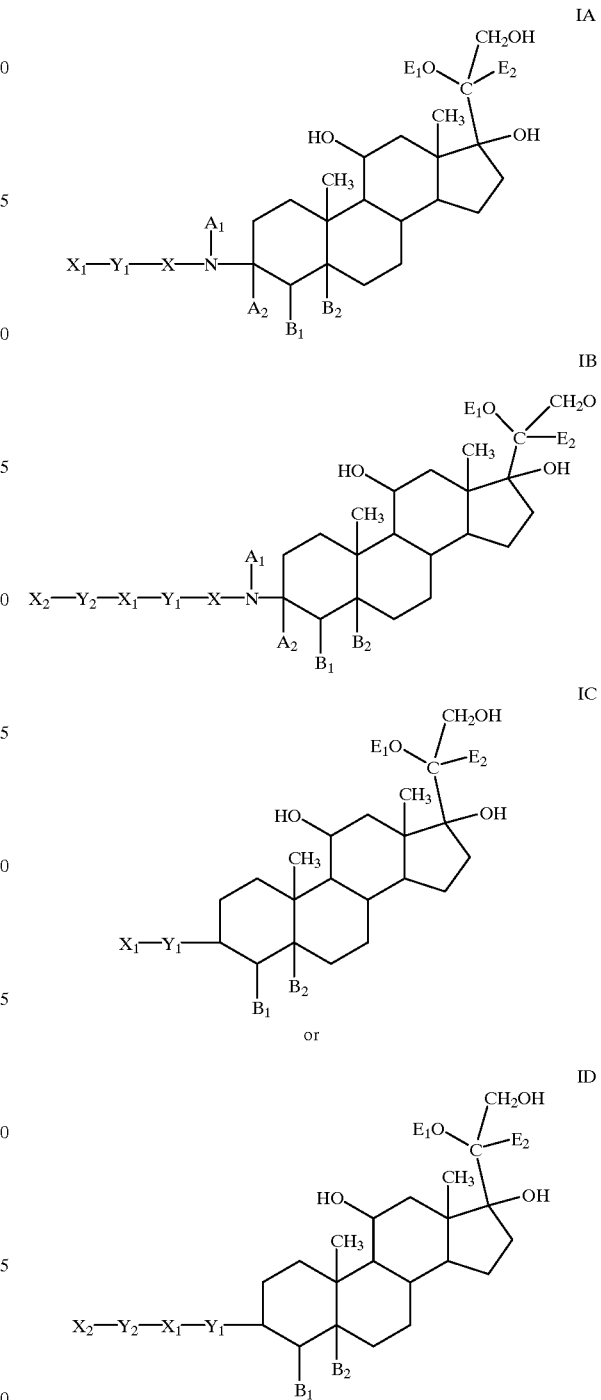

wherein X is O, S, sufonyl, or phosphono; X1 is a labeled or unlabeled natural or synthetic polymer or a label; Y1 is a linking group or a bond; X2 is a labeled or unlabeled natural or synthetic polymer or a label; Y2 is a linking group or a bond; A1 and A2 are each hydrogen or A1 and A2 together form a single bond, B1 and B2 are each hydrogen or B1 and B2 together form a single bond, E1 and E2 are each hydrogen or E1 and E2 together form a single bond provided at least one of A1 and A2, or B1 and B2, or E1 and E2 are each hydrogen and at least one of X1 or X2 is a labeled natural or synthetic polymer or a label, thereby forming labeled reduced cortisol conjugate that is bound and labeled reduced cortisol conjugate that is not bound to the immobilized or immobilizable receptor; and B) detecting either the labeled reduced cortisol conjugate that is bound or the labeled reduced cortisol conjugate that is not bound to the immobilized or immobilizable receptor as a measure of the amount of cortisol in the sample.

16. The method of claim 15 wherein X is O, and $X_1$ is bovine serum albumin.

17. The method of claim 16 wherein $Y_1$ is methylenecarbonyloxy and $X_2$ is a peroxidase.

18. The method of claim 17 wherein $X_2$ is a peroxidase and $Y_2$ is (4-[2,5-dioxo-3-{(2-ethylcarbonyl) sulfanyl}tetrahydro-1H-1-pyrrolyl]methyl)-1-cyclohexanecarbonyl and $X_2$ is horseradish peroxidase.

19. The method of claim 15 further comprising, separating the labeled reduced cortisol conjugate that is bound from the labeled reduced cortisol conjugate that is not bound to the immobilized or immobilizable receptor.

20. A method for performing a competitive binding assay for cortisol using a dry analytical element comprising a) a spreading zone,
b) one or more reagent zones,
c) a support, and together or separately in one or more of the zones, an immobilized receptor that binds cortisol and optionally, a labeled reduced cortisol conjugate of formula wherein X is O, S, sufonyl, or phosphono; $X_1$ is a labeled or unlabeled natural or synthetic polymer or a label; $Y_1$ is a linking group or a bond; $X_2$ is a labeled or unlabeled natural or synthetic polymer or a label; $Y_2$ is a linking group or a bond; $A_1$ and $A_2$ are each hydrogen or $A_1$ and $A_2$ together form a single bond, $B_1$ and $B_2$ are each hydrogen or $B_1$ and $B_2$ together form a single bond, $E_1$ and $E_2$ are each hydrogen or $E_1$ and $E_2$ together form a single bond provided at least one of $A_1$ and $A_2$, or $B_1$ and $B_2$, or $E_1$ and $E_2$ are each hydrogen and at least one of $X_1$ or $X_2$ is a labeled natural or synthetic polymer or a label, wherein the method comprises the steps of:

A) contacting the spreading zone of the dry analytical element with
   i) a sample suspected of containing cortisol, thereby forming cortisol that is bound and cortisol that is not bound to the immobilized receptor,
   ii) the labeled reduced cortisol conjugate if it is not present in the dry analytical element, thereby forming labeled reduced cortisol conjugate that is bound and labeled reduced cortisol conjugate that is not bound to the immobilized receptor, and B) detecting either the labeled reduced cortisol conjugate that is bound or the labeled reduced cortisol conjugate that is not bound to the immobilized receptor as a measure of the amount of cortisol in the sample.

21. The method of claim 20 wherein X is O, and $X_1$ is bovine serum albumin.

22. The method of claim 21 wherein $Y_1$ is methylenecarbonyloxy and $X_2$ is a peroxidase.

23. The method of claim 22 wherein $X_2$ is a peroxidase and $Y_2$ is (4-[2,5-dioxo-3-{(2-ethylcarbonyl)sulfanyl}tetrahydro-1H-1-pyrrolyl]methyl)-1-cyclohexanecarbonyl and $X_2$ is horseradish peroxidase.

24. The method of claim 20 further comprising, separating the labeled reduced cortisol conjugate that is bound from the labeled reduced cortisol conjugate that is not bound to the immobilized or immobilizable receptor.

25. A method for producing anti-cortisol antibodies comprising the steps of:
A) immunizing a host animal with a reduced cortisol conjugate of formula

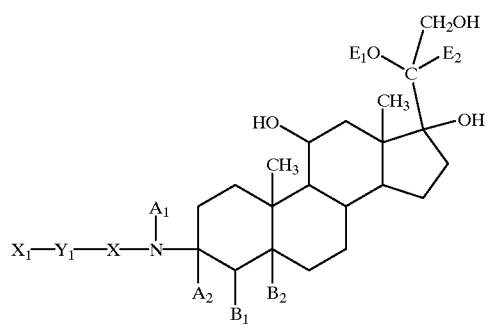

IA

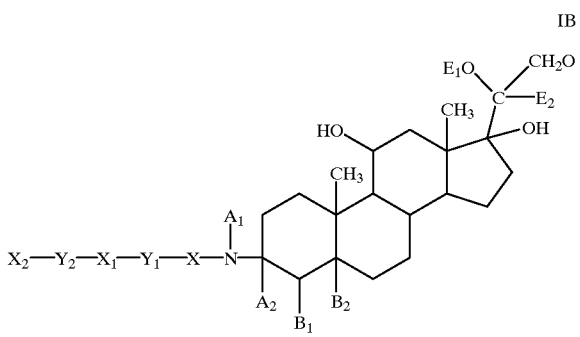

IB

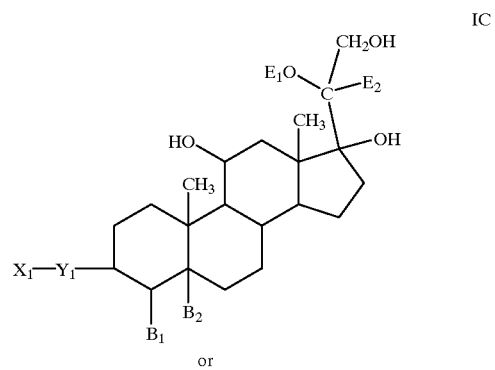

IC or

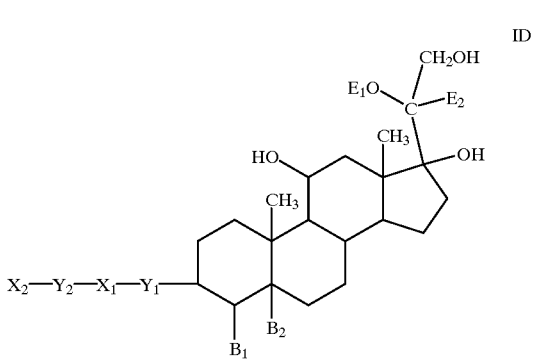

ID wherein X is O, S, sufonyl, or phosphono; $X_1$ is a labeled or unlabeled natural or synthetic polymer or a label; $Y_1$ is a linking group or a bond; $X_2$ is a labeled or unlabeled natural or synthetic polymer or a label; $Y_2$ is a linking group or a bond; $A_1$ and $A_2$ are each hydrogen or $A_1$ and $A_2$ together form a single bond, $B_1$ and $B_2$ are each hydrogen or $B_1$ and $B_2$ together form a single bond, $E_1$ and $E_2$ are each hydrogen or $E_1$ and $E_2$ together form a single bond provided at least one of $A_1$ and $A_2$, or $B_1$ and $B_2$, or $E_1$ and $E_2$ are each hydrogen, thereby producing antibodies that bind cortisol;

B) isolating the antibodies that bind cortisol from the blood serum or plasma of the host animal; or
C) removing the spleen, lymphatic tissue or other tissues or organs populated with antibody producing cells;
D) removing the antibody producing cells;
E) making hybridomas from the antibody producing cells;
F) selecting the hybridomas that produce antibody that binds cortisol; and
G) isolating the antibodies that bind cortisol.

* * * * *